United States Patent [19]

Phelps et al.

[11] Patent Number: 4,531,404
[45] Date of Patent: Jul. 30, 1985

[54] FLOW CELL ASSEMBLY

[75] Inventors: Craig H. Phelps, Dallas; Krishnaswamy Sampath, Carrollton, both of Tex.

[73] Assignee: Mobil Oil Corporation, New York, N.Y.

[21] Appl. No.: 566,727

[22] Filed: Dec. 29, 1983

[51] Int. Cl.$^3$ .............................................. G01M 3/02
[52] U.S. Cl. .......................................... 73/38; 277/12; 277/188 R
[58] Field of Search ............... 73/38; 277/165, 188 R, 277/12, 32

[56] References Cited

U.S. PATENT DOCUMENTS

| | | | |
|---|---|---|---|
| 2,534,718 | 12/1950 | Leas et al. | 73/38 |
| 2,676,485 | 4/1954 | Morgan | 73/38 |
| 3,120,967 | 2/1964 | Kazienko | 277/188 R X |
| 3,318,256 | 5/1967 | Green | 277/188 R |
| 3,329,006 | 7/1967 | Silkin | 73/38 |
| 3,425,716 | 2/1969 | Blau | 277/165 X |
| 3,548,634 | 12/1970 | Roy | 73/38 |
| 3,751,047 | 8/1973 | McGee | 277/165 |
| 3,945,650 | 3/1976 | Voitik | 277/165 |
| 4,258,902 | 3/1981 | Liebert et al. | 277/188 R X |

Primary Examiner—Kenneth M. Schor
Attorney, Agent, or Firm—McKillop Alexander J.; Michael G. Gilman; Charles J. Speciale

[57] ABSTRACT

A flow cell assembly for studying fluid flow through a disc-shaped sample, comprising inlet and outlet housings which are positioned on opposite sides of the test sample by means of sealing rings having a flat gasket which contacts the face of the test sample and an O-ring which contacts the inside edge of inlet and outlet chambers formed in the housings. Assembly is such that the housings are spaced apart when the sample is positioned therebetween. The peripheral outer edge of the sample is sealed against leaking by a coating of a two-part epoxy and/or a heat shrink material tape.

7 Claims, 2 Drawing Figures

FLOW CELL ASSEMBLY

BACKGROUND OF THE INVENTION

It is of interest in the scientific community to measure the fluid permeability and particularly the liquid permeability of various substances. Usually the substance to be tested is in the form of a very thin disc or wafer which is sometimes mounted against a foraminous support while being tested. One example of such testing is in a paper presented before the Society of Petroleum Engineers of AIME in Dallas, Tex. on Sept. 21-24, 1980 entitled "The Influence of Polymer Molecule-Wall Interactions on Mobility Control", Messrs. J. L. Duda et al of Pennsylvania State University described permeability modification of consolidated porous media by polymer solutions. (SPE Paper 9298) In the experiments described therein, a sample holder for porous media was used comprising a metal housing having an interior female thread and a male threaded cap which, when screwed into the female housing, contacted and compressed teflon gaskets on each side of a disc sample to be tested. It was not possible to visually observe the sample while such tests were being conducted.

The present invention is contemplated to be used for similar purposes, but to facilitate visual observation of the sample being tested. At the same time the present invention provides a sample holder which is also leak-tight and is yet simple and inexpensive to manufacture and to change the sample being tested.

SUMMARY OF THE INVENTION

The present invention is directed to a flow cell for holding a porous disc between two acrylic rings which are mounted in a chamber so as to allow flow of a fluid directly through the disc. The chambers of the cells are formed by two machined out centers of substantially identical inlet and outlet housings which have flanges which are bolted together about the disc assembly. The test sample disc is sealed on its top and bottom peripheral edges by acrylic rings which utilize rubber seals to prevent leakage between the rings and the housings and between the rings and the test sample. Preferably, the sealing is by means of a flat rubber gasket between the acrylic rings and the test sample and by means of O-rings between the acrylic rings and the respective housings.

Since the inlet and outlet housings do not touch each other, the peripheral edge of the test disc is visualy observably from the outside of the flow cell. However, this is a potential point of leakage of the test fluid so this peripheral edge is sealed, preferably with a two-part epoxy which is subsequently covered by a heat-shrink teflon tape.

This invention may be used to study the flow behavior of liquids through consolidated porous media. In particular, it may be used to investigate the penetration (transmissibility) thresholds of complexed polysaccharide solutions through well characterized porcelain discs under various conditions of flow rate and pressure drop. Such porcelain discs have well characterized uniform pores running mainly axially from face-to-face. The test discs are preferably about ½ thick and about 1-2" in diameter. These dimensions appear to be adequate for fully developed Darcy (laminar) flow to occur. Although many studies in the literature have used thin discs or wafers or filters to study such fluid flows, these porous media may give erroneous results if Darcy equation is employed in the analysis because transitional flows and end effects may dominate. Utilizing this invention to test discs of the present size appears to obviate this difficulty.

DESCRIPTION OF THE PREFERRED EMBODIMENT

Figure 1:
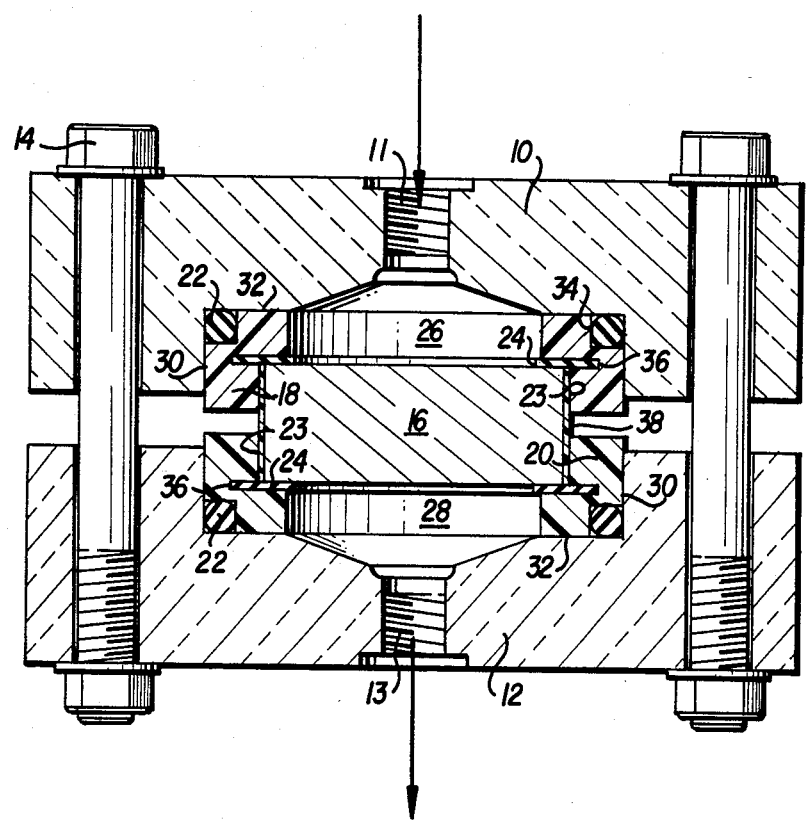
FIG. 1 is an elevational view, partially in section, of an assembled flow cell according to the present invention.

As shown in FIG. 1, which is given by way of example and illustration and not of limitation, the flow cell assembly of the present invention comprises an inlet housing 10, preferably made of a transparent plastics material, and a preferably identical outlet housing 12. These housings are held in facing but spaced apart relationship so that a flow path is defined from inlet 11 to outlet 13, generally through the center of the two housings and through test sample disc 16. The housings are held together by bolts and nuts 14, which may be torqued up to a sufficient degree to ensure that the disc-shaped test sample 16 is securely held in place in a leak-proof manner. Means are provided for holding the test sample between the housings, comprising an inlet housing acrylic ring 18 and an outlet housing acrylic ring 20. Each of these rings is generally "Z" shaped in cross-section, each ring having means for sealing the ring both against the housing and against the disc-shaped test sample 16 held therebetween.

The interior of each housing is hollowed out to form respectively an inlet chamber 26 and an outlet chamber 28. Each chamber has an outer peripheral margin defined by an axially extending outer face 30 and a radially extending inner face 32. These two faces meet at a corner in which there is positioned a first groove 34, which is formed by a square cutout of the axially and radially outward corner of each of the acrylic rings 18 and 20; these grooves 34 each house an O-ring 22. This O-ring is sized so that when positioned in its groove and the bolts 14 tighten to compress the housings together, the O-ring will be deformed preferably touching the groove walls and the faces 30 and 32 on all four of its sides. It should be understood that the rings 18 and 20 are preferably of an acrylic material which is not compressible and therefore the cross-sectional dimension of the O-ring is slightly greater than the height or width of the square groove 34 in which it is placed. The O-ring thus successfully performs a tight seal between chambers 26 or 28 and the remainder of the housing 10 or 12, preferably by slight deformation of the cross-sectional shape of the O-ring.

The sample test disc 16 is engaged and held in place by a second groove 23, which is cut out of the radially and axially inward corner of each ring 18 and 20. Each second groove 23 is closely fitted over the corners of the disc, which are defined by the flat faces of the disc meeting with the outer peripheral edge 38 of the disc 16.

Fluid leakage within second grooves 23 between the test disc 16 and the rings 18 and 20 is prevented by rubber gaskets 24, which are preferably in the form of flat washers which contact the flat upper and lower faces of disc 16, as shown in FIG. 1. In order to maintain gaskets 24 in their respective positions when the flow cell is disassembled, it is preferable to have the outer periphery of each gasket 24 extending into a third groove 36 radially outwardly of the edge of the disc 16.

As previously stated, it is preferable that housings 10 and 12 be made of a transparent plastics material, which also may be acrylic, so that the test sample and its influence on the fluid flows can be visually observed.

To preclude the possibility of fluid leakage going radially outwardly of the outer peripheral edge 38 of disc 16, this edge 38 is preferably covered by at least an epoxy adhesive material, preferably of the two-part type so that a good seal can be achieved. This epoxy would, of course, be applied and dried prior to inserting the sample into the flow cell so that no adhesion would take place between the test sample and the acrylic rings 18 and 20. Furthermore, for even more positive fluid sealing along the peripheral edge 38, it is preferable that the epoxy material be subsequently covered by a heat-shrink material, such as a teflon tape, so that even under higher pressures leakage would not take place.

Figure 2:
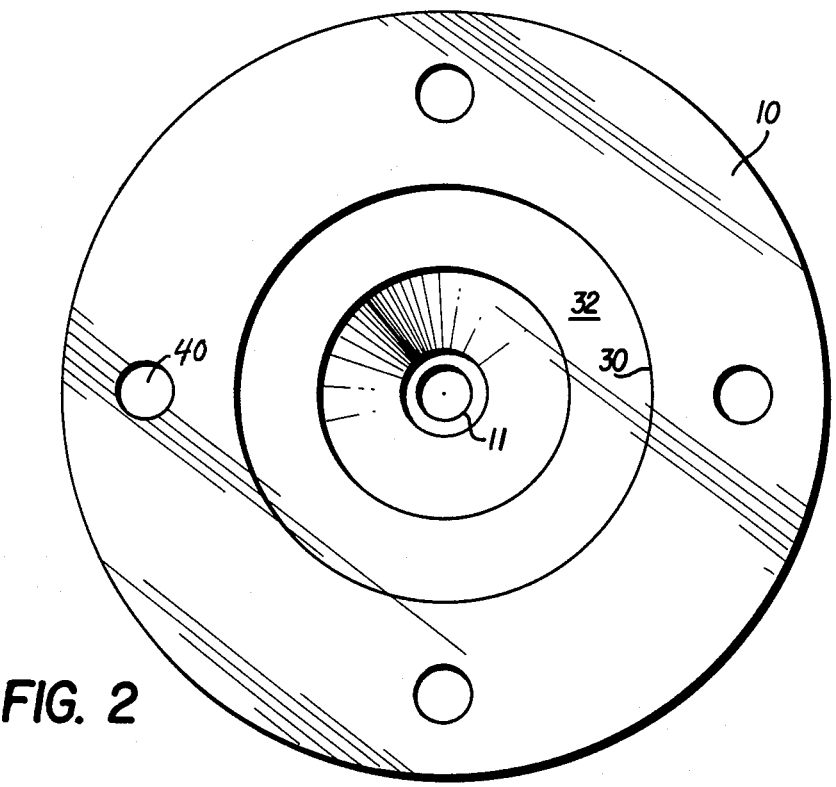
FIG. 2 is a plan view taken from above in FIG. 1, showing the general configuration of one of the housings.

In one embodiment of this invention, the test pressure was 180 psi with a working pressure of 100 psi and a working temperature of 50° C. The two housings were preferably held together by the four bolts through holes 40 (see FIG. 2), each being $\frac{1}{4}''$ in diameter and $3\frac{1}{2}''$ long. Each housing was made of the transparent acrylic material about 1" thick and $3\frac{3}{4}''$ in diameter. The inlet and exit chambers 26 and 28 were 2" in diameter, with a similar outside diameter for acrylic rings 18 and 20. Suitable connection means, such as screw or compression fittings, are provided on inlet 11 and outlet 13. The test samples, as previously stated, were porcelain discs having well characterized uniform pores running mainly axially from face-to-face. The discs were $\frac{1}{2}''$ thick and $1\frac{1}{2}''$ in diameter.

The foregoing description is furnished by way of example only to describe a preferred embodiment and the scope of the invention is defined by the claims which follow.

We claim:

1. A flow cell assembly for studying fluid flow through disc-shaped samples therein comprising:

an inlet housing and an exit housing of similar size and shape in facing and spaced apart relationship, each having a central cut-out portion defining respectively an inlet and outlet chamber; each chamber having an annular outer peripheral margin in mutual general axial alignment when the housings are in said facing and spaced apart relationship; each annular inner margin having an axially extending inner face and a radially extending inner face;

means for holding a disc-shaped test sample between said housings comprising a ring to fit in each margin, each ring having a radially and axially outward first groove holding a deformable O-ring against its respective margin and a radially and axially inward second groove shaped to fit over the edge of said disc-shaped sample to hold it in place between said housings;

a flat gasket on the face of said second groove which faces the flat face of said disc for seating said gasket against the flat face of said disc, around the circumference thereof, there being one gasket for each ring;

fastening means to secure said housings together and biased toward each other;

the arrangement being such that the housings are held spaced apart when assembled in confronting relationship with a disc-shaped sample therebetween, the peripheral edge of said disc, at least in the portion not covered by said rings, having a coating of an epoxy sealant or a heat shrink material to prevent leakage of test fluid from said peripheral edge.

2. The assembly of claim 1, in which said first groove is cut out of the corner of each said ring so that said O-ring contacts both the inner and outer faces of its respective margin.

3. The assembly of claim 1, in which said second groove has a radially outwardly extending third groove for holding said flat gasket in place.

4. The assembly of claim 1, in which the fastening means are screw threaded bolts in flanges in said housing radially outwardly of said rings.

5. The assembly of claim 1, in which the peripheral edge of said disc is coated with both a two-part epoxy sealant and a heat shrink material tape.

6. The assembly of claim 1, in which at least one of the housings is made of a transparent plastics material to facilitate visual observation of said test samples disc.

7. The assembly of claim 1, in which at least one of said rings is of an acrylic material.

* * * * *